(12) United States Patent
Borm et al.

(10) Patent No.: US 10,155,095 B2
(45) Date of Patent: Dec. 18, 2018

(54) METHOD AND APPARATUS FOR RESPIRATING OF PATIENTS

(75) Inventors: Pieter Borm, Eindhoven (NL); Bart Westerkamp, Alkmaar (NL)

(73) Assignee: LÖWENSTEIN MEDICAL TECHNOLOGY S.A., Luxembourg (LU)

( * ) Notice: Subject to any disclaimer, the term of this patent is extended or adjusted under 35 U.S.C. 154(b) by 1225 days.

(21) Appl. No.: 13/500,233

(22) PCT Filed: Oct. 6, 2010

(86) PCT No.: PCT/NL2010/000142
§ 371 (c)(1),
(2), (4) Date: Jun. 13, 2012

(87) PCT Pub. No.: WO2011/043650
PCT Pub. Date: Apr. 14, 2011

(65) Prior Publication Data
US 2012/0247467 A1    Oct. 4, 2012

(30) Foreign Application Priority Data

Oct. 7, 2009 (NL) .................................... 1037372

(51) Int. Cl.
*A61M 16/01* (2006.01)
*A61M 16/08* (2006.01)
*A61M 16/22* (2006.01)

(52) U.S. Cl.
CPC .......... *A61M 16/01* (2013.01); *A61M 16/085* (2014.02); *A61M 16/22* (2013.01)

(58) Field of Classification Search
CPC .......... A61M 16/0003; A61M 16/0045; A61M 16/0057; A61M 16/06; A61M 16/0063;
(Continued)

(56) References Cited

U.S. PATENT DOCUMENTS 5,694,924 A * 12/1997 Cewers .................... 128/204.21
5,857,458 A *  1/1999 Tham et al. ............. 128/203.28
(Continued)

FOREIGN PATENT DOCUMENTS

DE   102004033588 A1   2/2006

OTHER PUBLICATIONS

International Search Report for corresponding International Application No. PCT/NL2010/000142.

*Primary Examiner* — Gregory Anderson
*Assistant Examiner* — Elliot S Ruddie
(74) *Attorney, Agent, or Firm* — Egbert Law Offices, PLLC

(57) ABSTRACT

A method and apparatus for respirating a patient in which the apparatus has a circulation device for circulating a gas in one direction and a conduit system, a pressure control device for varying a pressure of the gas and the conduit system in accordance with the desired respirating pattern, a sensor for measuring a flow of the gas and a composition of the gas, at least one supply line for a component of the gas, and a discharge line connected to the conduit system. The discharge line has a first valve for discharging the gas out of the conduit system, a second valve behind the first valve and a third valve in spaced relation to a behind the second valve.

17 Claims, 1 Drawing Sheet

(58) Field of Classification Search
CPC .......... A61M 16/0066; A61M 16/0069; A61M 16/0075; A61M 16/01; A61M 16/22; A61M 16/1005; A61M 16/1015; A61M 2016/102; A61M 2016/1025; A61M 2016/103; A61M 2016/1035; A61M 16/104; A61M 16/12
See application file for complete search history.

(56) References Cited

U.S. PATENT DOCUMENTS

| | | | |
|---|---|---|---|
| 6,131,571 A * | 10/2000 | Lampotang et al. | 128/204.21 |
| 2004/0103899 A1* | 6/2004 | Noble | 128/207.18 |
| 2004/0216743 A1 | 11/2004 | Orr et al. | |
| 2009/0293872 A1* | 12/2009 | Bocke | 128/203.14 |

\* cited by examiner

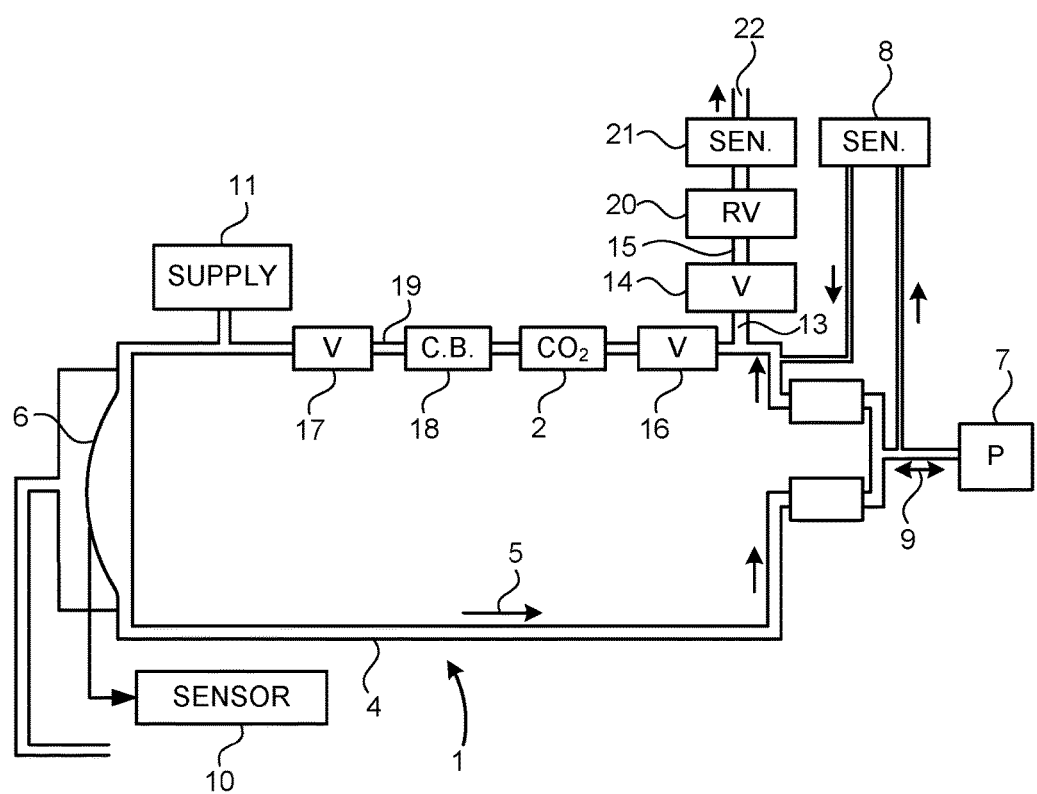

METHOD AND APPARATUS FOR RESPIRATING OF PATIENTS

CROSS-REFERENCE TO RELATED U.S. APPLICATIONS

Not applicable.

STATEMENT REGARDING FEDERALLY SPONSORED RESEARCH OR DEVELOPMENT

Not applicable.

NAMES OF PARTIES TO A JOINT RESEARCH AGREEMENT

Not applicable.

REFERENCE TO AN APPENDIX SUBMITTED ON COMPACT DISC

Not applicable.

BACKGROUND OF THE INVENTION

1. Field of the Invention

The present invention relates to a method for respirating of patients, whereby use is made of an apparatus which is provided with means for circulating a gas in one direction in a line or conduit system, with means for varying the pressure in the line system in accordance with a certain respirating pattern, with means for measuring the flow of the gas and the composition of the gas, whilst the line system is provided with connecting means for the patient and with one or more supplies for the various components of the respiratory gas, whereby the line system further is provided with a connecting means to a discharge line that is provided with a closing device for the discharge out of the line system of gas, whilst in the line system, as seen in the direction of the circulation of the gas, behind the connecting means to the discharge line a second closing means is provided.

2. Description of Related Art Including Information Disclosed Under 37 CFR 1.97 And 37 CFR 1.98

Such a method is known.

With the known method it is possible to switch from an open system, in which the patient again and again breathes in fresh breathing gas and the breathing gas exhaled by the patient is discharged completely out of the line system (non-rebreathing), to a half closed system, in which a part of the breathing gas exhaled by the patient is circulated once again and a part is discharged outside (some form of rebreathing).

The known method in the closed system has the drawback, that the "washing in" of the patient, that is to say the intake of anesthetic gas by the patient, takes a relatively long time. The patient among other things has nitrogen in his lungs, which has to be removed before the anesthetic can be started. To that end the patient is administered 100% oxygen until practically all nitrogen has been ventilated out of the lungs (the "washing" of the lungs with oxygen). In the closed system this takes much time, because each time the oxygen is inhaled together with a part of the gas that is already present. After the washing of the lungs of the patient with oxygen an anesthetic gas, here the carrier gas, such as xenon, is supplied, of which the patient takes in and exhales again a part. The amount of oxygen and xenon that is taken in is each time compensated with only xenon until the desired concentration of oxygen and the desired concentration of xenon is obtained in the breathing gas, which is the case only after a long time. The anesthetic or sedation here has to take place by other means.

In the half closed system a surplus of xenon, together with oxygen or not, is allowed to flow into the line system, by which the system gets to be overfilled. This is compensated by a "pop-off" system, in which a part of the gas in the system is discharged outside. Because of this the concentration of xenon increases. The more gas is supplied the faster the patient is washed in. This however leads to a substantial loss of gas.

It is an object of the invention to obviate this drawback of the known method.

BRIEF SUMMARY OF THE INVENTION

The method according to the invention to that end is characterized in that, as seen in the direction of circulation of the breathing gas, behind the second closing means and at a distance therefrom a third closing means is provided, in which the method comprises the following steps:

Opening of the first closing means, opening of the second and third closing means, feeding into the line system of a first gas, closing of the second and third closing means, feeding into the line system of the first gas, varying of the pressure in the line system in accordance with a certain respirating pattern for supplying to the patient of the first gas, feeding into the line system of a second gas, determining the arrival of the second gas at the mouth of the patient, closing of the first closing means and the opening of the second and third closing means or the opening of the second and third closing means and closing of the first closing means and the circulating in the system of the first and second gas.

According to a characteristic of the method according to the invention the first gas consists of oxygen or a mixture of oxygen and another gas.

According to a further characteristic of the method according to the invention the second gas consists of an elementary gas, such as for instance xenon, helium, argon or a composite gas, for instance laughing gas, or a mixture of a gas or gases with a vapour anesthetic.

According to a further characteristic of the method according to the invention the gas is circulated in the line system in such a way, that the duration of one circulation of the gas is 10 seconds at the most, more in particular 5 seconds at the most, more in particular 3 seconds a the most, and even more in particular 2.5 seconds at the most.

The invention further relates to an apparatus for the application of the method, which apparatus is provided with means for the circulating in one direction in a line or conduit system of a breathing gas, an anesthetic gas or a therapeutic gas, with means for varying the pressure in the line system in accordance with a certain respirating pattern, with means for measuring the flow of the gas and the composition of the gas, whilst the line system is provided with connecting means for the patient and with one or more supply lines for the various components of the respiratory gas and with means for withdrawing of the carbon dioxide exhaled by the patient in the line system, whereby the line system further is provided with a connecting means to a discharge line that is provided with a first closing device for the discharge out of the line system of breathing gas, whilst in the line system, as seen in the direction of the circulation of the gas, behind the connecting means to the discharge line a second closing means is provided, characterized in that, as seen in the direction of circulation of the breathing gas, behind the second closing means a third closing means is provided, whilst means are provided by means of which the second and third closing means can be controlled in such a way, that the section of the line system situated between the second closing means and the third closing means can be closed off, whilst the line system further is provided with means for the generating of a gas flow.

According to a characteristic of the apparatus according to the invention the capacity of the means for the generating of a gas flow is adapted to the volume of the line system in such a way, that the duration of one circulation of the gas is 10 seconds at the most, more in particular 5 seconds at the most, more in particular 3 seconds at the most, and even more in particular 2.5 seconds at the most.

According to a further characteristic of the apparatus according to the invention the means for the generating in the line system of a gas flow consist of a circulation blower.

According to another characteristic of the apparatus according to the invention the means for the generating in the line system of a gas flow are provided in the part of the line system that, as seen in the direction of the flow of the breathing gas, is situated behind the second closing means, and these are more in particular provided in the part of the line system that is situated between the second closing means and the third closing means.

With the method and apparatus according to the invention it is possible to wash in a patient in a quick and safe manner with the occurrence of no or only little loss of expensive gases.

Further characteristics and particulars of the method and apparatus according to the invention will be described with reference to the drawing of an example of an embodiment.

BRIEF DESCRIPTION OF THE SEVERAL VIEWS OF THE DRAWINGS

FIG. 1 is a schematic view of the apparatus of the present invention.

DETAILED DESCRIPTION OF THE INVENTION

In the example of an embodiment shown in the drawing the apparatus 1 is provided with means, among which the device 11 for the supplying of the various components of the respiratory gas, anesthetic gas or therapeutic gas, with means for circulating in one direction 5 in a line or conduit system 4 of respiratory gas, anesthetic gas or therapeutic gas, and with means 6 for varying the pressure in the line system 4 in accordance with a certain respirating pattern to allow the ventilation of the patient 7. Further in the line system 4 at the connecting means for the patient 7 means are provided, such as the apparatus 8, for the determination of the composition of the gas breathed in and the gas breathed out 9 by the patient. In the drawing is shown the principle of sampling removal. If so desired the gas that has been removed can be fed back into the system. It is also possible to make use of a measuring system directly in the gas breathed in and the gas breathed out 9. In the closed system by means of the sensor 10 the volume or the flow of the respiration by the patient can be measured, during spontaneous ventilation as well as during breathing upon the patient or in a given case supportive breathing upon the patient.

In the example of an embodiment shown the sensor 10 is provided in the part of the line system 4 that, as seen in the direction of circulation of the breathing gas, is situated behind the means 6 for varying the pressure in the line system.

The apparatus 11 provides the supply of the gases and the vaporous anesthetics into the system.

The line system 4 is provided with a connection 13 to a discharge line 15 provided with a first closing means, such as a first valve 14, for the discharge out of the line system 4 of respiratory gas.

In the line system 4, as seen in the direction of the circulation 5 of the gas, behind the connecting means 13 to the discharge line 15, a second closing means or second valve 16 is provided. Behind the second valve 16 in this example of an embodiment a circulation blower 18 and a carbon dioxide absorber 2 are provided. Behind this, as seen in the direction of circulation 5 of the breathing gas, a third closing means or third valve 17 is provided. The second valve 16 and the third valve 17 can be controlled in such a way, that the part 19 of the line system 4 situated therein between can be closed off from the circulation of the respiratory gas, and in this manner forms a closed off section in which a particular gas can be stored.

When the first valve 14 is closed no gas can escape the line system through the discharge line 15. When the valves 16 and 17 are open the breathing gas can flow freely to circulate in the line system. The system functions as a completely closed system.

When the first valve is 14 opened gas can be discharged through the discharge line 15 and the outlet 22 of the discharge line 15 out of the line system 4. Valve 16 and 17 are opened. The system functions as a half closed system. In the line system 4 the composition of the gas is measured (not shown in the drawing) while the flow of the gas evacuated through the outlet 22 of the discharge line 15 is measured by the sensor 20.

When the valve 14 is opened and the valves 16 and 17 are closed the system functions as an open system without rebreathing.

The system is prepared by blowing into the system a first gas, in this example of an embodiment pure oxygen, by means of the apparatus 11. The apparatus 11 is provided in the part of the line system that is situated behind the third valve 17.

The second valve 16 and the third valve 17 are open. Further the first valve 14 is open. Through the discharge 15 and the outlet 22 of the discharge 15 the gas is discharged out of the system. After this by means of the apparatus 11 the system is flushed with 100% oxygen. In the complete line system 95-100% oxygen now is present. After this the second valve 16 and the third valve 17 are closed. The system now functions as an open system. In the part 19 of the line system that is closed off more than 95% oxygen is present. The patient is now connected to the line system and the lungs subsequently are "washed clean" with 100% oxygen.

After this a second gas, an anesthetic gas, such as for instance xenon, or a second mixture of gases, is blown into the line system by the apparatus 11. After the washing clean one wants to obtain the correct concentration of the desired gas in the lungs of the patient in a quick and safe manner. By feeding into the line system 4 a mixture of oxygen and xenon the line system will be filled from the position of the apparatus 11 up to the patient 7 with oxygen and xenon. In the closed off section 19 only oxygen or substantially only oxygen will be present. In the part of the line system situated at the connection to the patient 7 the apparatus 8 is provided, by means of which at the mouth of the patient 7 the concentration of xenon is measured. In this manner it is determined when the line system 4 up to the patient 7 has become filled with a predetermined mixture of xenon/oxygen. When this is the case, the valve 14 is closed and the valves 16 and 17 are opened. The system now goes on to function as a closed system.

Instead of the measuring of the arrival of xenon at the mouth of the patient, and the afterwards closing of the valve 14 and the opening of the valves 16 and 17, one can also choose to feed by means of the apparatus 11 into the line system a predetermined amount of xenon and to subsequently close the valve 14 and to open the valves 16 and 17. In that case the switching of the valves 14, 16 and 17 does not take place in dependence of a measurement at the mouth of the patient.

After the system has gone on to function as a closed system the circulation blower 18 quickly mixes the gases in the closed off section 19 and the other part of the line system 4 with each other, through which the desired mixture is quickly obtained. To that end the circulation blower 18 is provided with a capacity that is such that by means of it a very fast mixing of the gases can take place. The circulation blower 18 has to circulate sufficiently so that the fastness of the mixing process is greater than the fastness of the processes within the human.

In this example of an embodiment the volume of the line system is 2.5 liter while in the line system a circulation blower 18 is provided with in this example of an embodiment a capacity of 60 liter per minute. This leads to a duration of one circulation of the gas of: 2.5 liter/60 liter/min=0.042 minutes=2.5 seconds.

Taking 2.5 seconds as a guiding principle, in the case of for instance a volume of the line system of 1.25 liter a circulation blower having a capacity of 30 liter per minute has to be applied, in the case of a volume of the line system of 5 liter a circulation blower having a capacity of 120 liter per minute has to be applied, and in the case of a volume of the line system of 0.625 liter a circulation blower having a capacity of 15 liter per minute has to be applied.

By the use of the circulation blower 18 a very fast mixing is obtained of the oxygen between the valves 16 and 17, the high percentage of oxygen in the lungs, the section between the patient and the first valve 14 filled with mainly oxygen and the section of the line system 4 between the apparatus 11 and the patient 7. Through this the necessity of prolonged washing is avoided, by which much of the special gas is lost, while a very short washing in time and a safe washing in are realised.

With the method and apparatus according to the invention the fast circulation by the circulation blower is of importance. The control of the composition of the respiratory gas by means thereof can be quicker than the processes in the human. Also because of this the intake of oxygen by the patient can be measured in an accurate manner.

With the closed system according to the invention it is further possible to wash quickly, through which the composition of the respiratory gas can be changed quickly. The apparatus 11 provides the supply of oxygen in the system and the supply of laughing gas. The pressure in the line system 4 is controlled by the means for the varying of the pressure. The flow through the discharge line 15 and the outlet 22 to outside is, in the half closed system, determined by the flow of fresh gas coming out of the apparatus 11, the movement of the means for the varying of the pressure and the position of the regulating valve 20 in de discharge line 15.

The regulating valve 20 in the discharge line 15 is intended to narrow or in the given case close at the moment the patient breathes in, so that the gas flow 5 does not become negative and the patient therefore only breathes in fresh gas. By means of the sensor 21 the volume or the flow of the gas flowing through the regulating valve 20 is measured.

It is further possible to replace, after the switching to the closed system, the amount of oxygen taken in by the patient by xenon only, and to decrease in this manner the concentration of oxygen and to proportionally increase that of xenon until the desired concentrations are reached. In this manner one saves on the "washing gas" that is discharged.

Instead of xenon any gas mixture can be taken, whereby the concentration of at least two gases can be chosen within narrow boundaries, for instance a xenon/helium mixture. By introducing xenon into the line system while the first valve 14 is open and the valves 16 and 17 are closed, determining the arrival of xenon at the mouth of the patient and subsequently closing the valve 14 and opening the valves 16 and 17 and to switch in this manner from the open to the closed system, there will occur no loss of xenon, while by means of the quick circulation and mixing a homogenous mixture quickly comes into being, and a very short washing in time and a safe washing in are obtained.

We claim:

1. A method for respirating a patient with an apparatus, the apparatus having a circulation device for circulating first and second gases in one direction in a conduit system, the apparatus having a pressure control device for varying a pressure of the first and second gases in the conduit system in accordance with a desired respirating pattern, the apparatus having a first sensor for measuring a flow of the first and second gases and a second sensor for measuring a composition of the first and second gases, the conduit system adapted to be connected to the patient, the conduit system having at least one supply line for a component of the first and second gases, the conduit system having a connection to a discharge line, the discharge line having a first valve for discharging the first and second gases out of the conduit system, the conduit system having a second valve downstream of the connection as viewed in a direction of the circulation of the first and second gases, the conduit system having a third valve in spaced relation to and downstream of the second valve as viewed in a direction of the circulation of the first and second gases, wherein a portion of the conduit system situated between the second valve and the third valve can be closed off from the circulation of respiration gas, the method comprising:
   opening the first valve and the second valve and the third valve;
   feeding the first gas into the conduit system;
   closing the second valve and the third valve;
   feeding the first gas into the conduit system after the step of closing the second and third valves;
   varying the pressure of the first gas in the conduit system in accordance with the desired respirating pattern of the patient;
   feeding the second gas into the conduit system;
   detecting an arrival of the second gas at the mouth of the patient;
   closing the first valve and opening the second and third valves; and
   circulating the first and second gases in the conduit system.

2. The method of claim 1, the first gas being oxygen or a mixture of oxygen and another gas.

3. The method of claim 1, the second gas selected from the group consisting of xenon, helium, argon, nitrous oxide and mixtures thereof.

4. The method of claim 1, the step of circulating being for a duration of no more than 10 seconds.

5. The method of claim 4, the duration being no greater than 2.5 seconds.

6. A respirating apparatus for administering an anesthesia or a therapeutic gas through inhalation by a patient, the respirating apparatus comprising:

a conduit system;
a circulation device cooperative with said conduit system so as to as to circulate the gas in one direction in said conduit system;
a pressure controlled device cooperative with said conduit system so as to vary a pressure of the gas in said conduit system in accordance with a respirating pattern of the patient;
a first sensor cooperative with said conduit system and adapted to measure a flow of the gas in said conduit system;
a second sensor cooperative with said conduit system and adapted to measure a composition of the gas in said conduit system;
a first connector connected to said conduit system so as to connect to the patient;
a second connector connected to said conduit system so as to connect said conduit system to at least one supply of the gas, the conduit system having a carbon dioxide absorber and adapted to withdraw carbon dioxide exhaled by the patient;
a discharge line connected by a connection to said conduit system, said discharge line having a first valve adapted to discharge breathing gas out of said conduit system;
a second valve cooperative with said conduit system and positioned in a location downstream of said connection to the discharge line as viewed in a direction of the circulation of the gas; and
a third valve cooperative with said conduit system and positioned in spaced relation downstream of said second valve as viewed in the direction of the circulation of the gas, said second and third valves being controllable such that a portion of said conduit system between said second and third valves can be closed off.

7. The respirating apparatus of claim 6, said circulation device adapted to circulate the gas for one circulation in said conduit system for a duration of no more than 10 seconds.

8. The respirating apparatus of claim 7, the duration being no more than 2.5 seconds.

9. The respirating apparatus of claim 6, the circulation device being a circulation blower.

10. The respirating apparatus of claim 6, said circulation device being positioned behind said second valve as seen in the direction of the circulation of the gas.

11. The respirating apparatus of claim 6, said second connector positioned behind said second valve as seen in the direction of the circulation of the gas.

12. The respirating apparatus of claim 6, said outlet for withdrawing carbon dioxide being positioned between said second and third valves.

13. The respirating apparatus of claim 6, said sensor positioned adjacent said first connector.

14. The respirating apparatus of claim 6, said first sensor positioned behind said pressure control device as seen in the direction of the gas.

15. The respirating apparatus of claim 6, said second sensor being positioned on or adjacent to said discharge line.

16. The respirating apparatus of claim 6, said discharge line having a regulating valve thereon.

17. The respirating apparatus of claim 15, said discharge line having another sensor thereon so as to measure a flow or volume of the gas through said discharge line.

* * * * *